US006746584B1

(12) United States Patent
Wang et al.

(10) Patent No.: US 6,746,584 B1
(45) Date of Patent: *Jun. 8, 2004

(54) OXYGEN SENSING DEVICE (75) Inventors: Da Yu Wang, Troy, MI (US); Paul Casey Kikuchi, Fenton, MI (US); Lone-Wen F. Tai, Rochester Hills, MI (US); David Sturge Eddy, Washington, MI (US); Raymond Leo Bloink, Swartz Creek, MI (US); Eric J. Detwiler, Davison, MI (US); Larry Max Oberdier, Royal Oak, MI (US)

(73) Assignee: Delphi Technologies, Inc., Troy, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/461,851

(22) Filed: Dec. 15, 1999

(51) Int. Cl.$^7$ ................................................ G01N 27/41
(52) U.S. Cl. .................. 204/425; 204/406; 204/427
(58) Field of Search ................... 204/425, 426, 204/427, 428, 429, 406; 205/783.5, 784, 785; 73/23.32

(56) References Cited

U.S. PATENT DOCUMENTS

| | | | | |
|---|---|---|---|---|
| 4,264,425 A | * | 4/1981 | Kimura et al. .............. 204/426 |
| 4,272,329 A | | 6/1981 | Hetrick et al. | |
| 4,302,312 A | * | 11/1981 | Ishitani et al. .............. 204/426 |
| 4,570,479 A | | 2/1986 | Sakurai et al. | |
| 4,722,779 A | * | 2/1988 | Yamada et al. .............. 204/410 |
| 4,769,124 A | * | 9/1988 | Okada et al. ................ 204/425 |
| 4,836,906 A | * | 6/1989 | Yamada et al. .............. 204/410 |
| 4,839,018 A | | 6/1989 | Yamada et al. | |
| 4,863,584 A | | 9/1989 | Kojima et al. | |
| 4,926,827 A | * | 5/1990 | Kato et al. ................... 204/406 |
| 5,221,445 A | * | 6/1993 | Wang et al. ................. 204/426 |
| 5,384,030 A | | 1/1995 | Duce et al. | |
| 5,467,636 A | | 11/1995 | Thompson et al. | |
| 5,602,325 A | | 2/1997 | McClanahan et al. | |
| 5,616,825 A | | 4/1997 | Achey et al. | |
| 5,733,504 A | | 3/1998 | Paulus et al. | |
| 5,762,737 A | | 6/1998 | Bloink et al. | |
| 5,849,165 A | * | 12/1998 | Kojima et al. .............. 204/429 |
| 6,096,187 A | * | 8/2000 | Mizoguchi et al. ...... 205/784.5 |

OTHER PUBLICATIONS

Logothetis et al "High–Temperature Oxygen Sensors Based on Electrochemical Oxygen Pumping", ACS Symposium Series 309, pp. 136–154, 1986.*

* cited by examiner

Primary Examiner—Kaj K. Olsen
(74) Attorney, Agent, or Firm—Jimmy L. Funke (57) ABSTRACT

A wide range oxygen sensor comprising a first oxygen pump cell, the first pump cell comprising: a first and a second electrode, with a first communication zone therebetween, the first electrode being exposed to exhaust gas, the second electrode being exposed to a heat source; and wherein at least one element of said first pump cell incorporates a gas-diffusion limiting characteristic; a second oxygen pump cell, operating at opposite polarity from said first oxygen pump cell, electrically isolated from said first oxygen pump cell, and disposed within a sensor substrate, the second cell comprising: a third and a fourth electrode, with a second communication zone therebetween, the third electrode being exposed to exhaust gas, the fourth electrode being exposed to a heat source; and wherein at least one element of said second pump cell incorporates a gas-diffusion limiting characteristic; at least one heating element for providing heat to said second electrode and said fourth electrode; and an electrical circuit for measuring the air-to-fuel ratio within the exhaust gas incident to said first and third electrodes.

46 Claims, 6 Drawing Sheets

OXYGEN SENSING DEVICE

TECHNICAL FIELD

The present invention relates generally to oxygen sensors. More particularly, the present invention relates to a novel design and configuration for improved sensing of wide range air-to-fuel ratios of exhaust gas.

BACKGROUND OF THE INVENTION

Oxygen sensors are used in a variety of applications that require qualitative and quantitative analysis of gases. For example, oxygen sensors have been used for many years in automotive vehicles to sense the presence of oxygen in exhaust gases, for example, to sense when an exhaust gas content switches from rich to lean or lean to rich. In automotive applications, the direct relationship between oxygen concentration in the exhaust gas and the air-to-fuel ratios of the fuel mixture supplied to the engine allows the oxygen sensor to provide oxygen concentration measurements for determination of optimum combustion conditions, maximization of fuel economy, and the management of exhaust emissions.

A conventional stoichiometric oxygen sensor typically consists of an ionically conductive solid electrolyte material, a porous electrode on the sensor's exterior exposed to the exhaust gases with a porous protective overcoat, and a porous electrode on the sensor's interior surface exposed to a known oxygen partial pressure. Sensors typically used in automotive applications use a yttria stabilized zirconia based electrochemical galvanic cell with porous platinum electrodes, operating in potentiometric mode, to detect the relative amounts of oxygen present in an automobile engine's exhaust. When opposite surfaces of this galvanic cell are exposed to different oxygen partial pressures, an electromotive force is developed between the electrodes on the opposite surfaces of the zirconia wail, according to the Nernst equation:

$$E = \left(\frac{-RT}{4F}\right)\ln\left(\frac{P_{O_2}^{ref}}{P_{O_2}}\right)$$

where:

$E$ = electromotive force $R$ = universal gas constant $F$ = Faraday constant $T$ = absolute temperature of the gas $P_{O_2}^{ref}$ = oxygen partial pressure of the reference gas $P_{O_2}$ = oxygen partial pressure of the exhaust gas Due to the large difference in oxygen partial pressures between fuel rich and fuel lean exhaust conditions, the electromotive force changes sharply at the stoichiomnetric point, giving rise to the characteristic switching behavior of these sensors. Consequently, these potentiometric oxygen sensors indicate qualitatively whether the engine is operating fuel rich or fuel lean, without quantifying the actual air to fuel ratio of the exhaust mixture. Increased demand for improved fuel economy and emissions control has necessitated the development of oxygen sensors capable of quantifying the exhaust oxygen partial pressure over a wide range of air fuel mixtures in both fuel-rich and fuel-lean conditions.

As taught by U.S. Pat. No. 4,863,584 to Kojima et al., U.S. Pat. No. 4,839,018 to Yamada et al., U.S. Pat. No. 4,570,479 to Sakurai et al., and U.S. Pat. No. 4,272,329 to Hetrick et al., an oxygen sensor which operates in a diffusion limited current mode produces a proportional output which provides a sufficient resolution to determine the air-to-fuel ratio under fuel-rich or fuel-lean conditions. Generally, diffusion limited current oxygen sensors have a pumping cell and a reference cell with a known internal or external oxygen partial pressure reference. A constant electromotive force, typically corresponding to the stoichiometric electromotive force, is maintained across the reference cell by pumping oxygen through the pumping cell. The magnitude and polarity of the resulting diffusion limited current is indicative of the exhaust oxygen partial pressure and, therefore, a measure of air-to-fuel ratio.

Where a gas-diffusion-limiting means is added to the oxygen pump, the pump current can be limited, and the limiting current is linearly proportional to the absolute value of the equilibrium oxygen concentration of the exhaust gas. In lean condition, the equilibrium oxygen concentration is larger than zero, which indicates a surplus of oxygen, and oxygen needs to be pumped out of the exhaust gas to create a limiting current. In the rich condition, the equilibrium oxygen concentration is smaller than zero, which indicates depletion of oxygen, and oxygen needs to be pumped into the exhaust gas to create a limiting current. Therefore, using the absolute value and the polarity of the limiting current, one can determine the air-to-fuel ratio of the exhaust gas.

However, an oxygen pump cell will not switch its current polarity automatically if both pump electrodes are exposed to the same exhaust gas. Conventional sensor technology either uses an air reference electrode as one of the pump electrodes or utilizes an air reference electrode as a third electrode to detect the lean or rich status of the exhaust gas (by emf mode) and to switch the current polarity accordingly. In this way, wide range air-to-fuel ratios of the exhaust gas can be determined.

Such conventional sensors use two types of air reference electrodes. The first type has a sizable air chamber to provide oxygen from an ambient air supply to the reference electrode. However, to avoid contamination by the exhaust gas, the air chamber requires a hermetic seal sensor package, which is expensive and is problematic in field applications.

The second type is a pumped-air reference electrode. It uses a pump circuit to pump oxygen from the exhaust gas to the reference electrode. As such, it does not require a sizable air chamber connected to ambient air. Nor does it require a hermetic seal sensor package. However, in addition to the pump circuit, the pumped-air reference electrode requires a gas transport mechanism for relieving the oxygen pressure built up at the reference electrode by the pumped-in oxygen. This gas transport mechanism provides relief from such pressure via connections to an ambient atmosphere source (either air or exhaust gas). If the gas transport mechanism is too restrictive, the sensing element is prone to pop or crack in field applications. If the gas transport mechanism is too relaxed, contamination of exhaust gasses flowing to the reference electrode will not be avoided.

Accordingly, there remains a pressing need in the art for a sensor that does not require the cost-prohibitive and problematic hermetic seal sensor packages with sizable air chambers. Further, there is a need for sensors that do not present gas transport problems commonly associated with pumped-air reference electrodes.

SUMMARY OF THE INVENTION

The problems and disadvantages of the prior art are overcome and alleviated by wide range oxygen sensor of the present invention, the sensor comprising a first oxygen pump cell, the first pump cell comprising: a first and a second electrode, with a first communication zone therebetween, the first electrode being exposed to exhaust gas, the second electrode being exposed to a heat source; and wherein at least one element of said first pump cell incorporates a gas-diffusion limiting characteristic; a second oxygen pump cell, operating at opposite polarity from said first oxygen pump cell, physically isolated from said first oxygen pump cell, and disposed within a sensor substrate, the second cell comprising: a third and a fourth electrode, with a second communication zone therebetween, the third electrode being exposed to exhaust gas, tile fourth electrode being exposed to a heat source; and wherein at least one element of said second pump cell incorporates a gas-diffusion limiting characteristic; at least one heating element for providing heat to said second electrode and said fourth electrode; and an electrical circuit for measuring the air-to-fuel ratio within the exhaust gas incident to said first and third electrodes.

BRIEF DESCRIPTION OF THE DRAWINGS

The present invention will now be described, by way of example only, with reference to the accompanying drawings which are meant to be exemplary, not limiting, and wherein like elements are numbered alike in several FIGURES, in which.

DESCRIPTION OF THE PREFERRED EMBODIMENT

The present invention relates to a unique, simplified, wide range oxygen sensor, comprising at least two oxygen pump cells operating under opposite polarity, each consisting of electrodes deposited around a conductive electrolyte, wherein at least one of said pump cells operates in a limiting current condition.

The double pump cell design of the present invention effectively eliminates the need for an air reference electrode having, alongside it, a sizable air chamber. Similarly, the present sensor is not encumbered by the limitations of problematic hermetically sealed sensor packaging. This is because the two cells within the sensor act in concert to prevent oxygen buildup and/or depletion at the inner electrodes. Further, where inner electrodes 24 and 34 are both exposed to exhaust gas by controlled porosity within the electrolyte 26 and 36, pressure buildup at the inner electrodes does not occur and the need for a sizable air chamber is eliminated.

In one embodiment of the present invention, the sensing of wide range air-to-fuel ratios of exhaust gas is achieved by using two isolated oxygen pump cells, both of which incorporate a gas-diffusion limiting mechanism or characteristic. The two pumps are operated in the same exhaust gas in opposite voltage polarity. Because the two cells work in opposite polarity, only one cell will be working in a current limiting mode, regardless of whether the exhaust gas is lean or rich. Accordingly, by identification of which cell is operating in a current limiting mode and by measurement of the amplitude of that limiting current, the air-to-fuel ratio of the exhaust gas can be determined.

Identification of which cell is in current limiting mode is done by comparison of the pump voltages or pump currents of the two pump cells. At constant applied pump voltage, the current limiting cell gives a smaller current. At constant pump current (where the cells are put in series), the current limiting cell creates a higher pump voltage. This measurement is done using electronic circuits.

Generally, the present embodiment may be made by any method known in the art such that two, isolated pump cells are placed in the same exhaust stream. The present invention relates to a unique configuration, including a dramatic simplification of air reference and packaging requirements over conventional designs. Accordingly, the present invention may be configured conventionally, as is known in the art, including, but not limited to, those described in commonly assigned U.S. Pat. Nos. 5,467,636 to Thompson et al., 5,602,325 to McClanahan et al., 5,616,825 to Achey et al., 5,384,030 to Duce et al., and 5,733,504 to Paulus et al., the relevant portions of which are hereby incorporated by reference.

More generally, the present invention relates to oxygen sensors constructed around a ceramic electrolyte, which conducts ionic oxygen. The electrolyte develops a voltage when the oxygen concentration on the two sides differs. To measure the oxygen concentration of the exhaust gas, one side of the electrolyte is exposed to the exhaust gas while the other side is kept in contact with air. The voltage across the electrolyte is a function of the difference in oxygen concentration.

Figure 1:
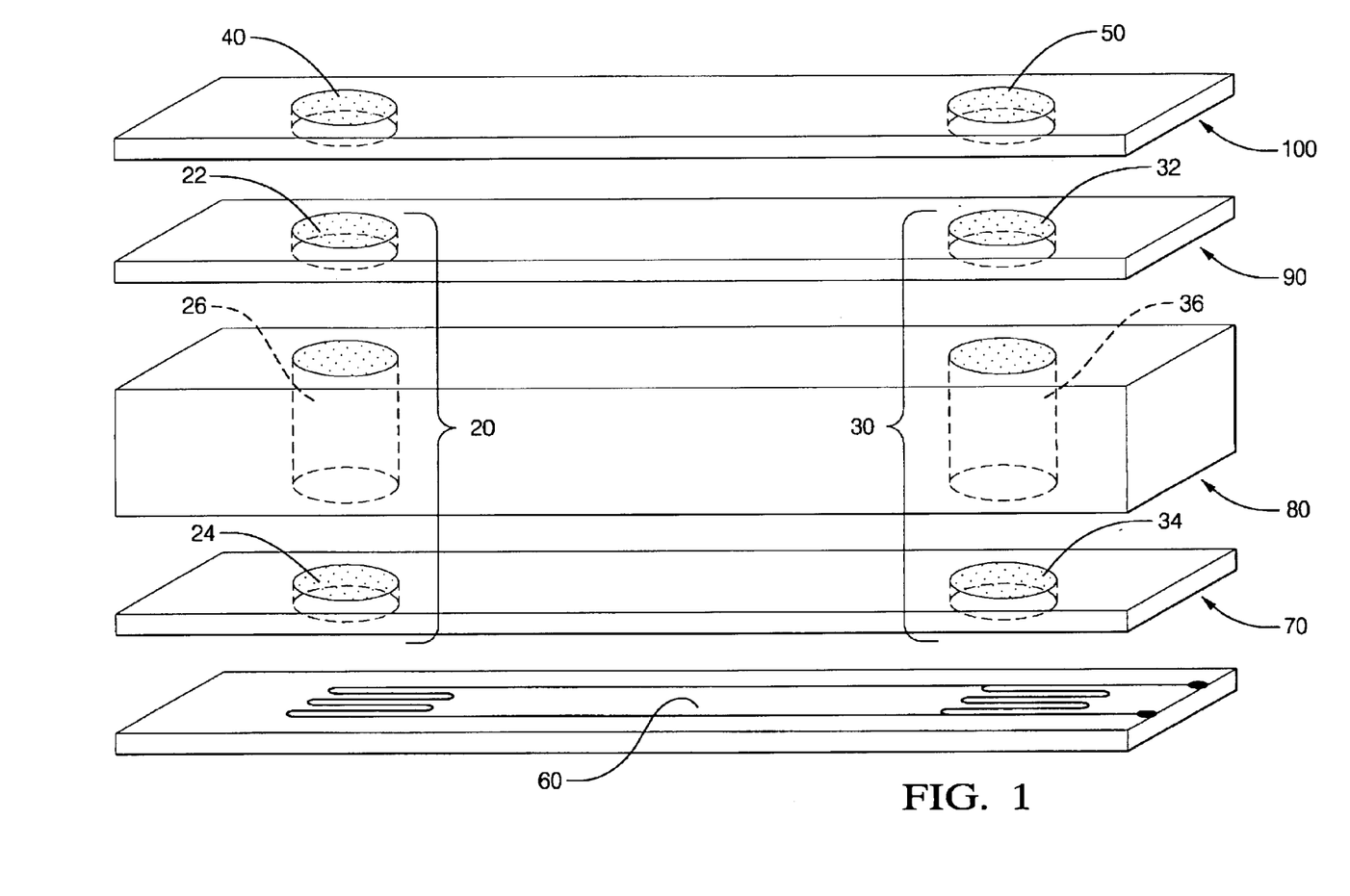
FIG. 1 is an expanded view of one embodiment of the present invention incorporating two isolated oxygen pump cells on the same side of an alumina heater.
Figure 2:
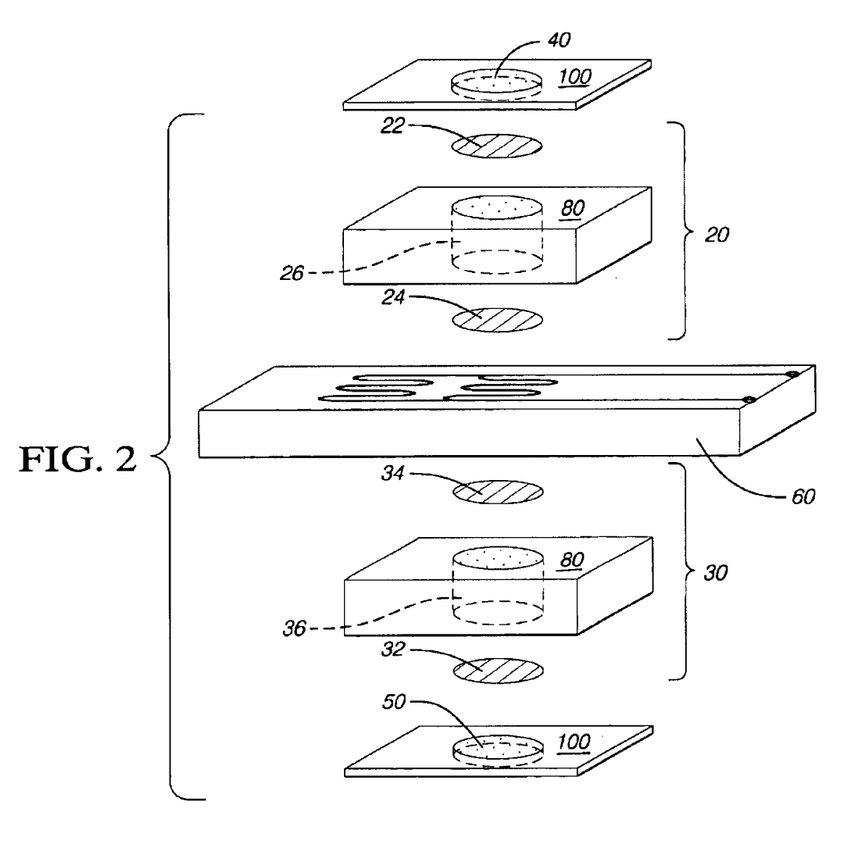
FIG. 2 is an expanded view of one embodiment of the present invention incorporating two isolated oxygen pump cells on opposite sides of an alumina heater.

Preferably, the sensor according to the present embodiment is configured according to either of FIG. 1 or 2. Both of those Figures show precisely the same sensor elements, only in different arrangements. Referring now to both of those Figures, pumping cell 20 is defined by electrodes 22 and 24, having disposed therebetween electrolyte 26. Similarly pumping cell 30 is defined by electrodes 32 and 34, having disposed therebetween electrolyte 36. As used herein, electrodes 24 and 34 are inner electrodes and electrodes 22 and 32 are exhaust electrodes. Poison resistance layers 40 and 50 are preferably disposed above electrodes 22 and 32, respectively, between electrodes 22 and 32 and the exhaust gasses. Alumina heating element 60 can be disposed adjacent the inner electrodes opposite electrolytes 26 and 36.

FIG. 1 shows both of cells 20 and 30 disposed on the same side of alumina heating element 60. Pumping cells 20 and 30 are completely isolated from each other by the remainder materials of layers 70, 80, 90, and 100. Such materials generally are dielectric materials that effectively protect various portions of the sensor while functioning as separators and substrates. Layers 70, 80, 90, and 100 physically isolate pumping cells 20 and 30. Layer 100 further acts to physically cover layer 90 and outer electrodes 22 and 32 and to provide physical protection, e.g., against abrasion, and to electrically isolate these components from the packaging.

Preferably, these layers are comprised of material having substantially similar coefficients of thermal expansion, shrinkage characteristics and chemical compatibility in order to at least minimize, if not eliminate, delamination and other processing problems. Typically these layers are composed of alumina or another dielectric material capable of inhibiting electrical communication and providing physical protection. Layer thickness is not a critical factor and is only optimized taking into account manufacturing concerns. Accordingly, it is preferred that the layers are up to about 250 microns thick with a thickness of about 10 to about 250 microns preferred. These layers can be formed using ceramic tape casting methods or other methods such as plasma spray deposition techniques, screen printing, stenciling and others conventionally used in the art.

The various electrodes disposed in layers 70 and 90 can be comprised of any catalyst capable of ionizing oxygen, including, but not limited to, noble metal catalysts such as platinum, palladium and others, including alloys. The electrodes should possess porosities sufficient to permit the diffusion of oxygen and exhaust gas molecules therethrough and a thickness sufficient to attain the desired catalytic activity. Porosity should be sufficiently great as not to substantially restrict gas diffusion. Typically, porosity equal to or greater than the porosity of the porous electrolyte and a thickness of approximately 1.0 to about 25 microns can be employed, with a thickness of about 10 to about 20 microns preferred.

The electrodes can be formed using conventional techniques such as sputtering, chemical vapor deposition, screen printing, and stenciling, among others, with screen printing the electrodes onto appropriate tapes preferred due to simplicity, economy, and compatibility with the subsequent co-fired process.

Figure 5:
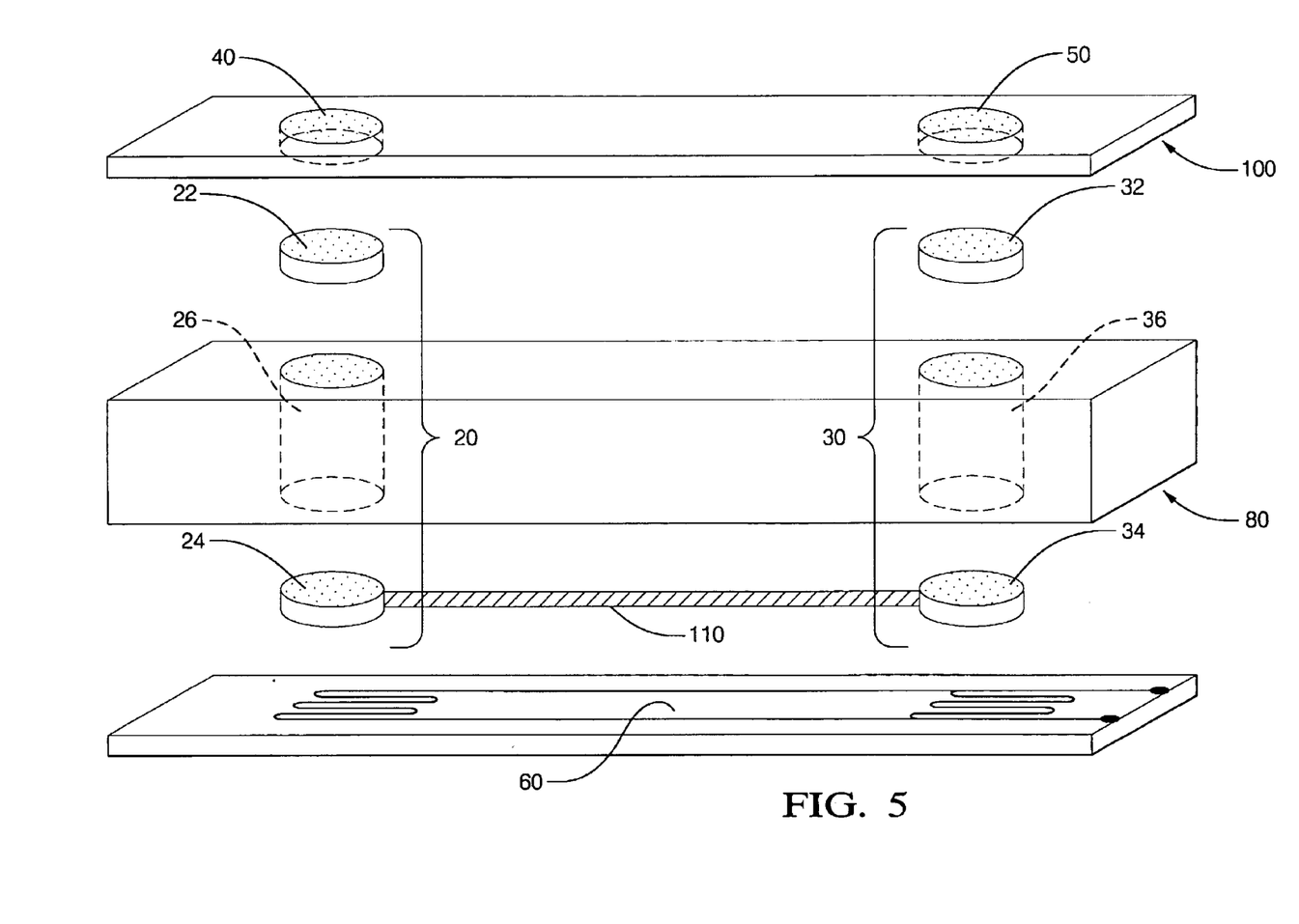
FIG. 5 is an expanded view of another embodiment of the present invention incorporating two oxygen pump cells, connected by a gas chamber between the inner electrodes of both pump cells.
Figure 6:
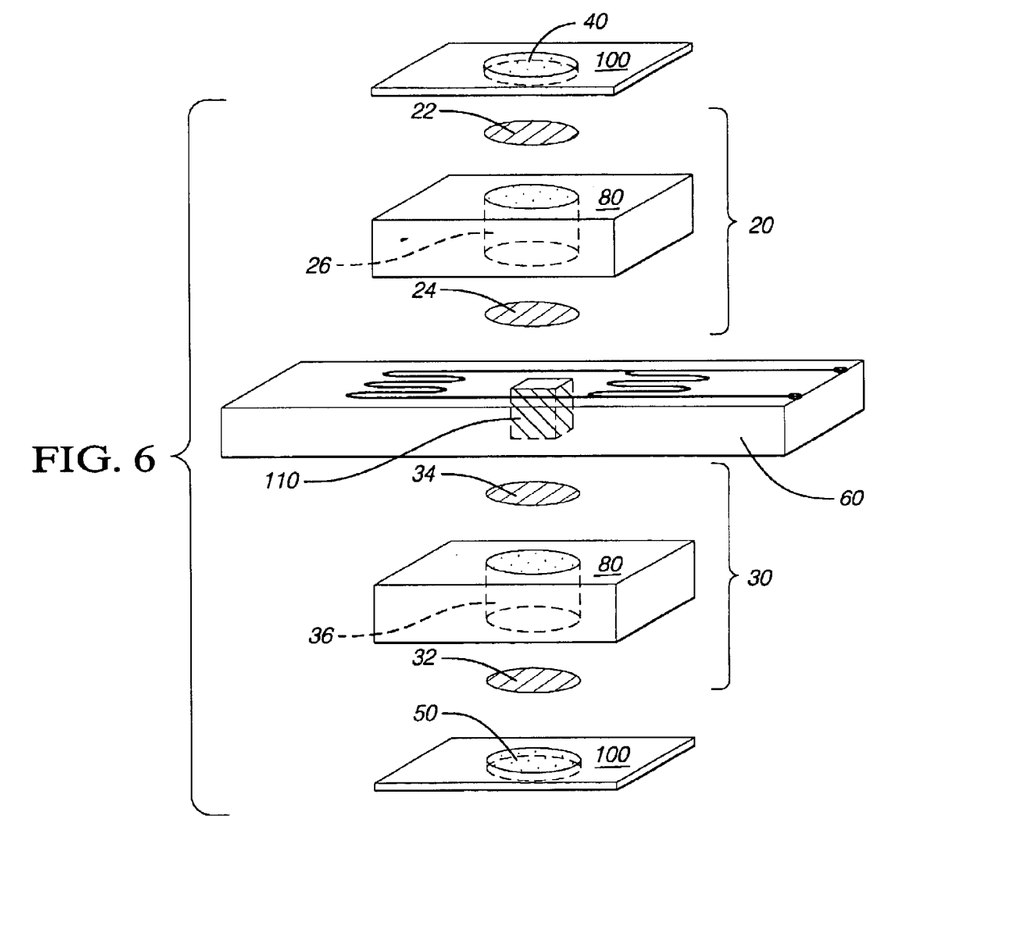
FIG. 6 is an expanded view of an embodiment of the present invention incorporating two oxygen pump cells with a shared gas chamber, but wherein the two oxygen pump cells are located on opposite sides of an alumina heater.

FIGS. 2, 5, and 6 show the preferred electrode configuration. In these Figures, layers 70 and 90 are eliminated, and the electrodes are deposited or screen printed directly onto the exposed electrolyte 26, 36 within layer 80. layers 100 and 60 are then fired with, pressure laminated onto, or otherwise fabricated to layer 80, such that the materials of layers 60, 80, and 100 completely insulate the electrode materials.

Layer 100 includes porous protective areas 40, 50 disposed over electrodes 22 and 32 to prevent poisoning of the electrodes. Typically, the electrodes are coated with a porous ceramic to stop erosion of the electrodes and to smooth the flow of the exhaust gasses to eliminate noise due to turbulent gas flow. Such porous protective area may optionally include a lead gettering layer (not shown) disposed between the exhaust electrodes 22 and 32 and the porous protective areas 40 and 50 or within the porous protective areas themselves. Such is preferably used where poisoning of the electrode by lead content in the exhaust stream is a concern.

Where included, the lead gettering material should comprise a material that will not contaminate the exhaust electrodes 22 and 32 during processing or in operation. The material preferably has a sufficient porosity to enable the passage of the exhaust gases at the given material thickness, including catalytic materials, such as platinum, palladium, rhodium, or transition metals; and non-catalytic materials, such as nickel or titanium; among other materials, and alloys and mixtures thereof. Metals are preferred lead gettering materials, with platinum especially preferred because it does not contaminate the electrode and because it can be fired in air at high temperatures. The gettering layer (not shown) preferably comprises about 10 volume% to about 100 volume% platinum printed from about 2 micrometers to about 50 micrometers thick, with about 10 micrometers to about 14 micrometers preferred to allow a sufficient quantity of the exhaust gases to pass through the gettering layer.

The electrolyte materials 26 and 36 of the oxygen pumps can be made of oxide conducting materials, including materials having controlled porosity. Such suitable materials include any material capable of permitting the electrochemical transfer of oxygen ions while inhibiting the physical passage of any exhaust gases, which preferably also has an ionic/total conductivity ratio of approximate unity, and which is compatible with the environment in which the sensor will be utilized. Possible electrolyte materials include conventional materials Such as zirconia based materials, e.g., yttria stabilized zirconia, calcia stabilized zirconia, and magnesia stabilized zirconia, silica stabilized zirconia, and alumina stabilized zirconia, among others and other materials as well as mixtures and alloys thereof.

Typically, electrolytes 26 and 36 have thicknesses of up to about 500 microns with thicknesses of approximately 25 microns to about 500 microns preferred. This layer can be formed via many conventional processes including, but not limited to, die pressing, roll compaction, stenciling and screen printing. For limited process compatibility, it is preferred to form all of the pump materials, including the electrolyte bodies 26 and 36, into buttons having similar geometries which are subsequently joined with alumina or electrolyte thick film tapes (such tapes, which are used as layer substrates for layers 70, 80, 90, and 100, are preferably made by slurry cast method).

It was described above that for the present embodiment, both isolated oxygen pump cells incorporate a gas-diffusion limiting mechanism. This gas-diffusion limiting mechanism may be incorporated into any of the poison resistance protection layers 40 and 50, electrodes 22, 24, 32, and 34, and/or the electrolytes 26 and 36. Where this gas-diffusion limiting mechanism is incorporated, as is preferred, into the electrolytes 26 and 36, such electrolytes should have a controlled porosity sufficient to enable the physical movement of exhaust gas therethrough, while limiting the current output of the oxygen sensor under relatively extreme fuel-rich or fuel-lean conditions. This is preferred in that where the gas-diffusion limiting mechanism is incorporated in electrolytes 26 and 36, the electrodes surrounding those electrolytes 26 and react with exhaust gas at substantially the same time, thereby improving response performance.

Typically the porosity ranges up to about 20%, with a median pore size of up to about 0.5 microns. Commonly assigned U.S. Pat. No. 5,762,737 to Bloink et al., which is hereby incorporated by reference, further explains the porous electrolyte. Alternatively, one or both of electrolytes 26 and 36 can be a solid electrolyte having one or more perforations, holes, slits, or apertures therein so as to enable the physical passage of exhaust gases.

Similarly, where the gas-diffusion limiting mechanism is incorporated into electrodes 22 and 32, or 24 and 34, or into poison resistance layer 40 and 50, such materials should have a controlled porosity sufficient to enable the physical movement of exhaust gas therethrough, while limiting the current output of the oxygen sensor under relatively extreme fuel-rich or fuel-lean conditions. As described above, gas-diffusion limiting mechanism may alternatively or additionally be in the form of perforations, holes, slits, or apertures.

The heat source or heater 60 can be any conventional heater capable of maintaining the oxygen sensor at a sufficient temperature to facilitate the various electrochemical reactions therein. Typically the heater, which is a metal such as platinum, platinum-alumina, palladium, platinum-palladium, among others, or alloys thereof, or another material having sufficient heat transfer characteristics, is generally screen printed onto a dense alumina substrate to a thickness of about 5 to about 50 microns.

Fabrication of the above described layers and elements is preferably finalized by thermal-pressure lamination of all the above layers, having the preferred button-joint elements of the pump cell components installed therein, and by firing of the combined layers as is known in the art.

FIG. 2 shows another embodiment of the present invention, wherein isolated cells 20 and 30 disposed on opposite sides of heating element 60. As in FIG. 1, sensor components are surrounded by dense alumina material (70 in FIG. 1) or by an electrolyte material such that direct contact of electrodes 22 and 24 with exhaust gasses is made only through poison resistance protection layers 40 and 50. With the exception of the configurational difference, i.e. one cell being on the opposite sides of alumina heating element 60, materials and fabrication of such materials is substantially as described above.

Figure 3:
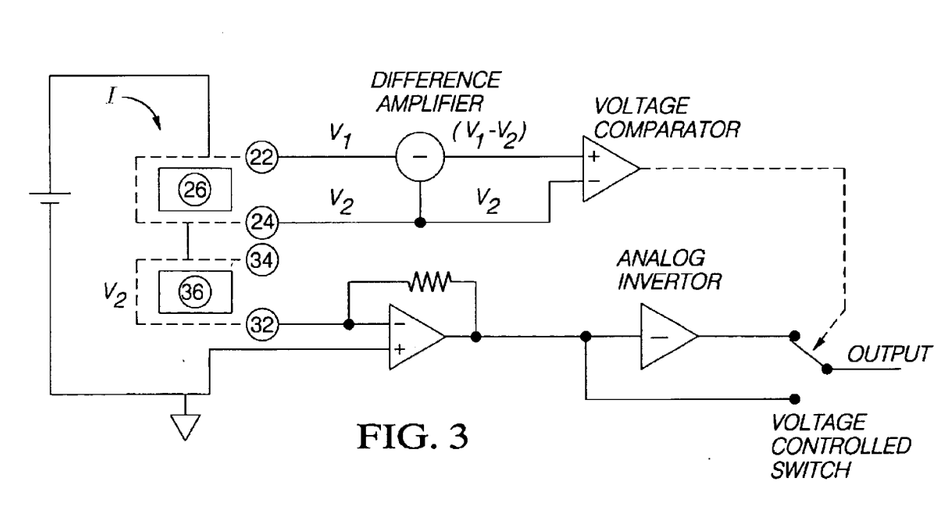
FIG. 3 is a circuit box diagram of a circuit suitable for identifying the current limiting pump and measuring the voltage difference between tile first and second pump cells.

For operation of either of the configurations in FIGS. 1 and 2, the two pump cells 20 and 30 may either be placed in series or in parallel. It should he noted that these are merely alternate means of measuring the same signals. Accordingly, there is not a general preference for either electrical configuration. An exemplary embodiment of an electrical configuration, comprising the electrodes placed in series, is shown in FIG. 3. Electrical configurations may be of any components known in the art arranged to identify the current limiting pump and to measure the absolute magnitude of the pump circuit polarity. For simplicity, the configuration discussed below is preferred.

Figure 4A:
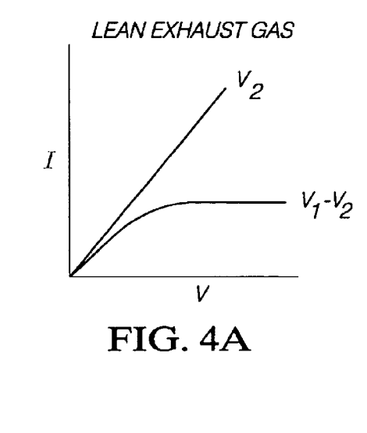
FIG. 4a is a graph showing the voltage and current characteristics of the first and second pump cells in lean exhaust gas.
Figure 4B:
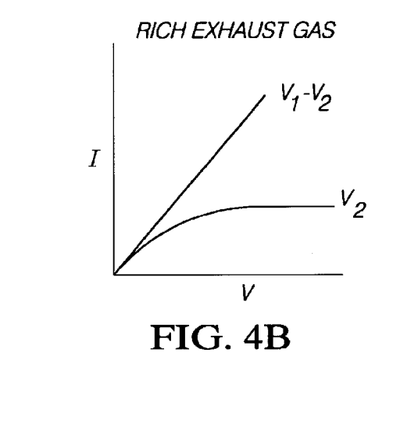
FIG. 4b is a graph showing the voltage and current characteristics of the first and second pump cells in rich exhaust gas.

As shown in FIG. 3, the two pump cells are placed in series and operated at constant voltage. To optimize sensitivity of the pump measurements, such voltage is preferably less that about 2 volts. Because the oxygen pumps operate in opposite polarity, the pump current is limited by only one of the two pumps according to the lean-rich condition of the exhaust gas. Behavior of the pump current across each of cells 20 and 30 are shown in FIGS. 4a and 4b for lean exhaust gas and rich exhaust gas, respectively. For the circuit box diagram in FIG. 3, $V_1 - V_2$ corresponds to the potential difference across cell 20, and $V_2$, corresponds to the potential difference across cell 30.

As can be seen from FIGS. 4a and 4b, the current limiting mode is always associated with a higher voltage (at same current level) or a smaller current (at same voltage). Therefore, although the pump current as arranged in FIG. 3 will always have the same polarity, by comparing $V_1$ and $V_2$ of the two pump cells, identification of the current limiting pump cell can be ascertained. This is done, in FIG. 3, with a voltage comparator, used in conjunction with a difference amplifier, to control a voltage controlled switch. This switch, in turn, controls the polarity of the output signal. Based on output polarity, and based on the absolute magnitude of that polarity, the air-fuel ratio of the exhaust gas is measured.

In another embodiment of the present invention, only the first pump cell 20 has a gas-diffusion limiting mechanism, which provides enough current limiting capability to allow the first pump cell to operate in the interested range of air-to-fuel ratios. With reference to FIGS. 5 and 6, the positive electrode 24 of the first pump cell 20 is isolated from exhaust gas, and the negative electrode 22 is exposed to exhaust gas moving through the poison protective layer 40. Disposed between the positive, inner electrode 24 of the first cell 20 and inner electrode 34 (either positive or negative) of the second cell 30 is a gas chamber 110, which itself is isolated from exhaust gas. Electrode 32 of cell 30 may be exposed either to air, if practicable, or exhaust gas filtered through poison protection layer 50.

The pump current of cell 30 is controlled by pump cell 20 through a feedback loop control circuit. An exemplary circuit may be seen in FIG. 7. The control circuit controls the pump current of the pump cell 30 such that pump cell 30 operates at an equal current but with opposite polarity. Thus, electrode 34 of pump cell 30, which connects to electrode 24 of pump cell 20 through the gas chamber, pumps oxygen in and out of the shared gas chamber 110 opposite to that of electrode 24. This allows pump cell 20 to sense the air-fuel ratio of the exhaust gas in current limiting mode without accumulation or depletion of oxygen at positive electrode 24. As such, this feature eliminates the requirement that a mechanism for releasing pressure be attached to positive electrode 24, as would otherwise be needed.

As in the previous embodiments, the present embodiment can be in any configuration as is known in the art. FIGS. 5 and 6 provide exemplary embodiments. Similarly, materials and fabrication methods are substantially as was described above with the exception of incorporation of the gas chamber linking electrodes 24 and 34 or indeed electrodes 24 and 32, if practicable. This gas chamber 110 can be made by any method such as is commonly known in the art, including burning away or cutting away of ceramic substrate material between electrode 24 and one of electrodes 34 and 32, among others. However, the gas chamber 110 is preferably formed by disposing a fugitive material conforming to the desired shape and path of the gas chamber 110.

All that need be done is to provide some connectivity between electrode 24 and one of electrodes 34 and 32. As such, the gas chamber 110 need only be large enough and direct enough to provide a minimal connection for the two cells 20 and 30 to work in concert. Fugitive material, which will, after firing, be consumed to form a cavity, should be laid in a thickness and along a path to satisfy the minimal requirement that the two electrodes be connected. As with the other components of the sensor, the fugitive material, as with the above compounds, may be deposited along the desired path by known procedure, including, but not limited to, screen printing, die pressing, stenciling, ceramic tape casting, or other method. As can be seen in the exemplary embodiment of FIG. 5, this is preferably done either on or adjacent to layer 70 between electrodes 24 and 34. In FIG. 6, this is preferably done through the layer containing heater 60 such that the gas chamber is not exposed to outside exhaust gases and between electrodes 24 and 34.

This fugitive material may be any material that will be consumed during the sensor preparation process, including, but not limited to, organic compounds, such as graphite, camphor and carbon, among others. Small particulate carbon, such as carbon black or graphite, is preferred because it is inexpensive, typically has a low level of impurities, is not easily ignited, and is non-poisonous. The thickness of the fugitive material should be sufficient to form a cavity effective to allow interaction of gases between electrode 24 and one of electrodes 34 and 32. To optimize production costs, the fugitive material is preferably up to about 150 microns thick, with between about 12 microns to about 38 microns particularly preferred.

Other than through the gas chamber disposed between electrode 24 and electrode 34, the pump cells are isolated as described above for FIGS. 5 and 6. This can be seen in FIG. 7, which shows an exemplary control circuit. In general, the oxygen pump cell is operated at a voltage designed to maximize pump cell sensitivity. There, oxygen pump cell 20 is typically operated at less than about 2 volts, preferably operated at a voltage of less than about 1 volt, and with particular preference between about 0.45 and 0.55 volts.

Figure 7:
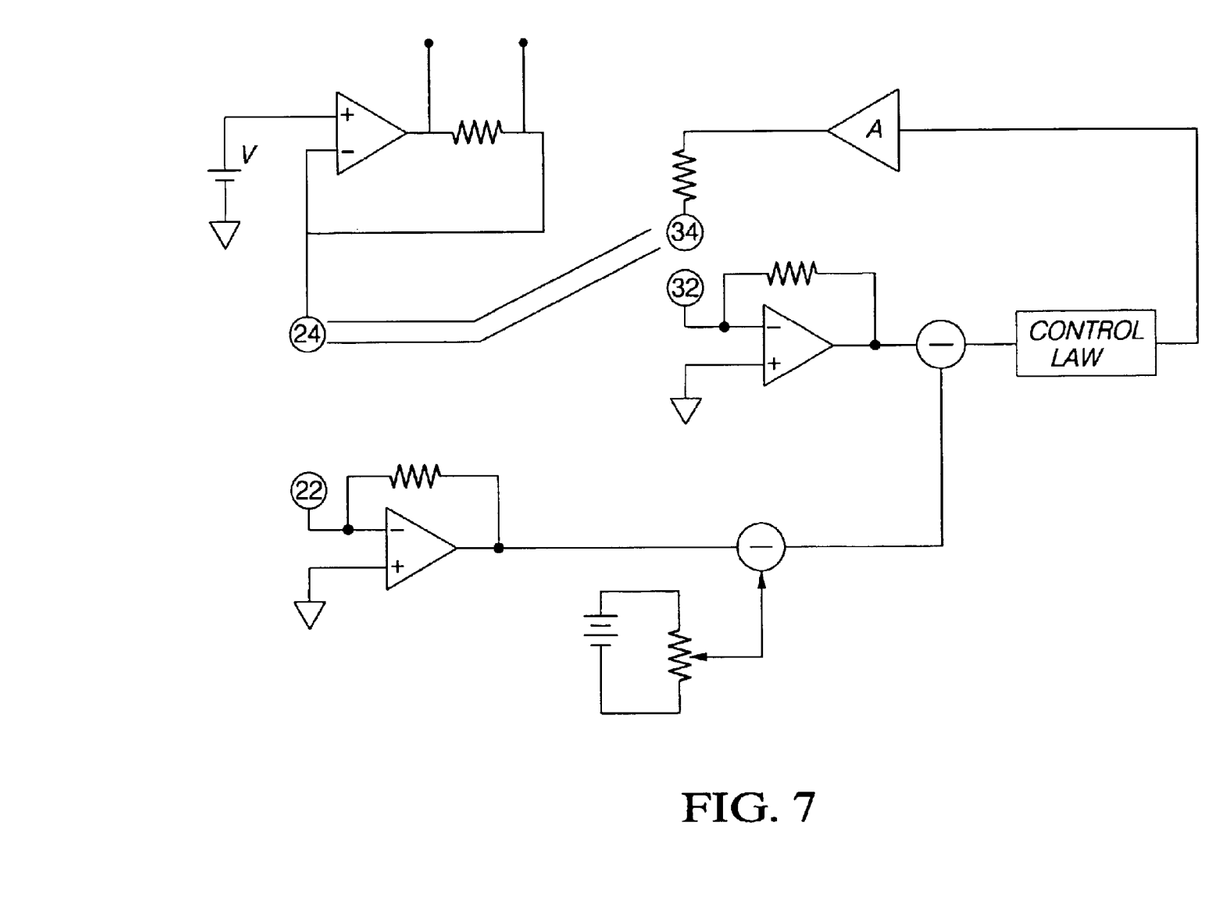
FIG. 7 is a circuit box diagram showing a suitable circuit for measuring the air-to-fuel ratio within the exhaust gas incident to said first and third electrodes and for controlling the current of the second pump cell so as to be equal in amplitude but opposite in polarity from said first pump cell.

The air-fuel ratio of the exhaust gas is determined by measuring the limiting current drawn through electrodes 22 and 24 of pump cell 20. As shown in FIG. 7, the control circuit uses the limiting current from pump cell 20 to control pump cell 30 such that an equal amount of current is generated at opposite polarity between electrodes 32 and 34 of pump cell 30. The control law box in FIG. 7 represents the circuit that compares the absolute values of the pump currents in both pumps, that compares the two pump cell polarities, and that directs the proportional-integral-derivative (PID) control. The PID control then directs pump cell 30 to pump the same amount of current at opposite polarity such that the effect of pump cell 20 on the accumulation or depletion of oxygen at electrode 24 is nullified by action of pump cell 30.

The present invention advantageously makes available a unique, simplified, wide range oxygen sensor that effectively eliminates the need for an air reference electrode having, alongside it, a sizable air chamber. Similarly, sensors of the present invention are unencumbered by the limitations of problematic hermetically sealed sensor packaging. Elimination of this expensive requirement translates directly to reduced product cost and increased product life.

What is claimed is:

1. An oxygen sensor, comprising:
   not more than two electrochemical cells;
   wherein one of said cells comprises a first oxygen pump cell further comprising: a first and a second electrode, with a first communication zone therebetween, said first electrode being exposed to exhaust gas, said second electrode being exposed to a heat source, and wherein said first pump cell comprises a gas-diffusion limiting characteristic configured to enable the physical movement of exhaust gas therethrough and limit the current output of the oxygen sensor;
   wherein said other of said cells comprises a second oxygen pump cell, capable of operating at opposite polarity from said first oxygen pump cell and physically isolated from said first oxygen pump cell, said second oxygen pump cell further comprising: a third and a fourth electrode, with a second communication zone therebetween, said third electrode being exposed to exhaust gas, and said fourth electrode being exposed to said heat source, and wherein said second pump cell comprises a gas-diffusion limiting characteristic configured to enable the physical movement of exhaust gas therethrough and limit the current output of the oxygen sensor; and
   an electrical circuit for measuring an air-to-fuel ratio within said exhaust gas incident to said first and third electrodes.

2. The sensor of claim 1, wherein said first oxygen pump cell further comprises a poison protective layer disposed adjacent to and in contact with said first electrode to protect such first electrode.

3. The sensor of claim 2, wherein said poison protective layer is a ceramic material with a porosity sufficient to permit diffusion of oxygen and exhaust gas molecules therethrough.

4. The sensor of claim 2, wherein said poison protective layer is a ceramic material having sufficient perforations, holes, slits, or other apertures to enable physical passage of exhaust gases.

5. The sensor of claim 1, wherein said second oxygen pump cell further comprises a poison protective layer disposed adjacent to and in contact with said third electrode.

6. The sensors of claim 5, wherein said poison protective layer is a ceramic material with a porosity sufficient to permit diffusion of oxygen and exhaust gas molecules therethrough.

7. The sensor of claim 6, wherein such ceramic material porosity is sufficient to enable the physical movement of exhaust gas therethrough, while limiting current output of said oxygen sensor under relatively fuel-rich or fuel-lean conditions.

8. The sensor of claim 5, wherein said poison protective layer is a ceramic material having sufficient perforations, holes, slits, or other apertures to enable physical passage of exhaust gases.

9. The sensor of claim 8, wherein the apertures of said poison protective are sufficient so as to enable physical passage of exhaust gases, while limiting current output of said oxygen sensor under relatively fuel-rich or fuel-lean conditions.

10. The sensor of claim 1, wherein said first and second communication zones comprise an oxide conducting electrolyte, suitable for permitting electrochemical transfer of oxygen ions while inhibiting physical passage of exhaust gases.

11. The sensor of claim 10, wherein said electrolyte materials is yttria stabilized zirconia, calcia stabilized zirconia, magnesia stabilized zirconia, silica stabilized zirconia, alumina stabilized zirconia, or a combination thereof.

12. The sensor of claim 10, wherein said electrolyte material of at least one of said first and second pump cells comprises said gas-diffusion limiting characteristic.

13. The sensor of claim 12, wherein said gas-diffusion limiting characteristic comprises a controlled porosity of the electrolyte material, and wherein said porosity is up to about 20%, with a median pore size of up to about 0.5 microns.

14. The sensor of claim 12, wherein said gas-diffusion limiting characteristic comprises one or more perforations, holes, slits, or apertures formed in said electrolyte material.

15. The sensor of claim 1, wherein said first, second, third, and fourth electrodes comprise a catalyst capable of ionizing oxygen, and wherein said electrodes are of a thickness of up to about 25 microns.

16. The sensor of claim 15, wherein said first, second, third, and fourth electrodes is a noble metal catalyst.

17. The sensor of claim 16, wherein said noble metal catalyst is platinum, palladium or an alloy thereof.

18. The sensor of claim 1, wherein at least one of said first and second electrodes comprises a gas-diffusion limiting mechanism sufficient to enable physical movement of exhaust gas or oxygen therethrough, while limiting the output of said pump cell under fuel-rich or fuel-lean conditions.

19. The sensor of claim 18, wherein said gas-diffusion limiting characteristic comprises a controlled porosity of the electrode material, and wherein said porosity is up to about 20%, with a median pore size of up to about 0.5 microns.

20. The sensor of claim 18, wherein said gas-diffusion limiting characteristic comprises one or more perforations, holes, slits, or apertures formed in electrolyte material.

21. The sensor of claim 1, wherein at least one of said third and fourth electrodes comprises said gas-diffusion limiting characteristic sufficient to enable physical movement of exhaust gas or oxygen therethrough, while limiting current output of the pump cell under fuel-rich or fuel-lean conditions.

22. The sensor of claim 21, wherein said gas-diffusion limiting characteristic comprises a controlled porosity of said electrode material, and wherein said porosity is up to about 20%, with a median pore size of up to about 0.5 microns.

23. The sensor of claim 21, wherein said gas-diffusion limiting characteristic comprises one or more perforations, holes, slits, or apertures formed in said electrolyte material.

24. The sensor of claim 1, wherein said sensor substrate comprises at least one substrate comprising a dielectric material capable of inhibiting electrical communication.

25. The sensor of claim 24, wherein said substrate is composed of alumina.

26. The sensor of claim 25, wherein said substrate is composed of a plurality of joined layers of material, each layer being up to about 200 microns thick.

27. The sensor of claim 24, wherein said substrate is composed of a plurality of joined layers of material, each layer being up to about 200 microns thick.

28. An oxygen sensor, comprising:
  not more than two electrochemical cells;
  wherein one of said cells comprises a first oxygen pump cell, disposed within a first substrate, further comprising: a first, negative electrode and a second, positive electrode, with a first communication zone therebetween, said first electrode being exposed to exhaust gas, said second electrode being exposed to a heat source; and wherein said first pump cell comprises a gas-diffusion limiting characteristic;
  wherein the other of said cells comprises a second oxygen pump cell, physically isolated from said first oxygen pump cell and disposed within said first substrate or a second substrate, and further comprising: a third electrode and a fourth electrode, with a second communication zone therebetween, said third electrode being exposed to exhaust gas, said fourth electrode being exposed to said heat source;
  a gas chamber, isolated from exhaust gases and connecting said second, positive electrode of said first pump cell and said fourth electrode of said second pump cell; and
  an electrical circuit for measuring an air-to-fuel ratio within said exhaust gas incident to said first and third electrodes and for controlling the current of the second pump cell.

29. The sensor of claim 28, wherein said first oxygen pump cell further comprises a poison protective layer disposed over said first electrode, said poison protective layer capable of permitting the diffusion of oxygen and exhaust gas therethrough.

30. The sensor of claim 29, wherein said oxygen pump cell further comprises a poison protective layer disposed over said third electrode, said poison protective layer permitting the diffusion of oxygen and exhaust gas therethrough.

31. The sensor of claim 29, wherein said poison protective layer is a ceramic material that limits the current output of said oxygen sensor under relatively fuel-rich or fuel-lean conditions.

32. The sensor of claim 28, wherein said second oxygen pump cell further comprises a poison protective layer disposed over said third electrode, said poison protective layer permitting the diffusion of oxygen and exhaust gas therethrough.

33. The sensor of claim 32, wherein said poison protective layer is a ceramic material.

34. The sensor of claim 28, wherein said first and second communication zones comprise an oxide conducting electrolyte, suitable for permitting the electrochemical transfer of oxygen ions while inhibiting the physical passage of any exhaust gases.

35. The sensor of claim 34, wherein said electrolyte material is yttria stabilized zirconia, calcia stabilized zirconia, magnesia stabilized zirconia, silica stabilized zirconia, alumina stabilized zirconia, or a combination thereof.

36. The sensor of claim 28, wherein said first, second, third, and fourth electrodes comprise a catalyst capable of ionizing oxygen, and wherein said electrodes are of a thickness of up to about 25 microns.

37. The sensor of claim 36, wherein said first, second, third, and fourth electrodes are noble metal catalysts.

38. The sensor of claim 37, wherein said noble metal catalyst is platinum, palladium or alloys thereof.

39. The sensor of claim 37, wherein said gas-diffusion limiting characteristic comprises one or more perforations, holes, slits, or apertures formed in the electrolyte material.

40. The sensor of claim 28, wherein said first electrode comprises said gas-diffusion limiting characteristic sufficient to enable the physical movement of exhaust gas or oxygen therethrough, while limiting the current output of the pump cell under fuel-rich or fuel-lean conditions.

41. The sensor of claim 40, wherein said gas-diffusion limiting characteristic comprises a controlled porosity of the electrode material and wherein said porosity is up to about 20%, with a median pore size of up to about 0.5 microns.

42. The sensor of claim 28, wherein said first substrate and said second substrate comprise a dielectric material capable of inhibiting electrical communication.

43. The sensor of claim 42, wherein said first substrate and said second substrate are composed of alumina.

44. The sensor of claim 43, wherein said first substrate and said second substrate comprise a plurality of joined layers of material, each layer being up to about 200 microns thick.

45. The sensor of claim 42, wherein said first substrate and said second substrate comprise a plurality of joined layers of material, each layer being up to about 200 microns thick.

46. An oxygen sensor, comprising:
  not more than two electrochemical cells;
  wherein one of said cells comprises a first oxygen pump cell further comprising: a first and a second electrode, with a first communication zone therebetween, said first electrode being exposed to exhaust gas, said second electrode being exposed to a heat source, and wherein said first pump cell comprises a gas-diffusion limiting characteristic;

wherein the other of said cells comprises a second oxygen pump cell, capable of operating at opposite polarity from said first oxygen pump cell and physically isolated from said first oxygen pump cell, said second oxygen pump cell further comprising: a third and a fourth electrode, with a second communication zone therebetween, said third electrode being exposed to exhaust gas, and said fourth electrode being exposed to said heat source, and wherein said second pump cell comprises a gas-diffusion limiting characteristic; and an electrical circuit for measuring an air-to-fuel ratio within the exhaust gas incident to said first and third electrodes, wherein the electrical circuit both identifies a current limiting pump and measures a voltage difference at constant current or a current difference at constant voltage between said first and second oxygen pump cells.

* * * * *